US012478418B2

(12) United States Patent
Shelton, IV et al.

(10) Patent No.: US 12,478,418 B2
(45) Date of Patent: Nov. 25, 2025

(54) RECLAMATION PACKAGING FOR SURGICAL INSTRUMENT AND RELATED METHODS

(71) Applicant: Cilag GmbH International, Zug (CH)

(72) Inventors: Frederick E. Shelton, IV, Hillsboro, OH (US); Jacqueline C. Aronhalt, Loveland, OH (US); Taylor W. Aronhalt, Loveland, OH (US); Cameron D. McLain, Deer Park, OH (US); Nicholas J. Ross, Franklin, OH (US)

(73) Assignee: Cilag GmbH International, Zug (CH)

( * ) Notice: Subject to any disclaimer, the term of this patent is extended or adjusted under 35 U.S.C. 154(b) by 737 days.

(21) Appl. No.: 17/854,114

(22) Filed: Jun. 30, 2022

(65) Prior Publication Data

US 2024/0000491 A1 Jan. 4, 2024

(51) Int. Cl.
*A61B 18/00* (2006.01)
*A61B 34/30* (2016.01)
(Continued)

(52) U.S. Cl.
CPC .............. *A61B 18/00* (2013.01); *A61B 34/30* (2016.02); *A61B 2018/00178* (2013.01);
(Continued)

(58) Field of Classification Search
CPC .......... A61B 2018/00964; A61B 2018/00988; A61B 34/30; A61B 2050/005;
(Continued)

(56) References Cited

U.S. PATENT DOCUMENTS 5,374,813 A 12/1994 Shipp
7,354,440 B2 4/2008 Truckai et al.
(Continued)

FOREIGN PATENT DOCUMENTS

CN 202682045 U 1/2013
CN 102909184 A 2/2013
(Continued)

OTHER PUBLICATIONS

International Search Report and Written Opinion dated Oct. 23, 2023, for International Application No. PCT/IB2023/056625, 14 pages.
(Continued)

*Primary Examiner* — Linda C Dvorak
*Assistant Examiner* — Bradford C. Blaise
(74) *Attorney, Agent, or Firm* — Frost Brown Todd LLP

(57) ABSTRACT

A surgical kit includes a surgical instrument, a packaging, and a return packaging. The packaging defines an interior and an exterior in a closed configuration. The surgical instrument is disposed within the interior of the packaging or coupled with the packaging in the closed configuration. The packaging is configured to transition to an open configuration by a user to expose the interior and allow for access of the surgical instrument during a surgical procedure. The return packaging is configured to receive at least a portion of the surgical instrument after the surgical procedure for reduced cross-contamination. The return packaging is at least one of coupled with the packaging or disposed within the interior in the closed configuration.

20 Claims, 10 Drawing Sheets

(51) Int. Cl.

| | |
|---|---|
| ***A61B 50/00*** | (2016.01) |
| ***A61B 50/30*** | (2016.01) |
| ***A61B 50/36*** | (2016.01) |

(52) U.S. Cl.

CPC ......... *A61B 2050/005* (2016.02); *A61B 50/30* (2016.02); *A61B 2050/3008* (2016.02); *A61B 50/36* (2016.02)

(58) Field of Classification Search

CPC ............ A61B 50/30; A61B 2050/3006; A61B 2050/3007; A61B 2050/3008; A61B 2050/314; A61B 2050/318; A61B 50/36

See application file for complete search history.

(56) References Cited

U.S. PATENT DOCUMENTS

| | | | | |
|---|---|---|---|---|
| 7,381,209 | B2 | 6/2008 | Truckai et al. | |
| 8,319,134 | B2 | 11/2012 | Blomeyer | |
| 8,663,220 | B2 | 3/2014 | Wiener et al. | |
| 8,820,605 | B2 | 9/2014 | Shelton, IV | |
| 9,125,662 | B2 | 9/2015 | Shelton, IV | |
| 9,314,308 | B2 | 4/2016 | Parihar et al. | |
| 9,949,785 | B2 | 4/2018 | Price et al. | |
| 10,624,709 | B2 | 4/2020 | Remm | |
| 10,835,307 | B2 | 11/2020 | Shelton, IV et al. | |
| 11,229,471 | B2 | 1/2022 | Shelton, IV et al. | |
| 11,690,642 | B2 | 7/2023 | Black et al. | |
| 2003/0163287 | A1* | 8/2003 | Vock | A61B 5/1112 702/187 |
| 2006/0079874 | A1 | 4/2006 | Faller et al. | |
| 2007/0191713 | A1 | 8/2007 | Eichmann et al. | |
| 2008/0200940 | A1 | 8/2008 | Eichmann et al. | |
| 2012/0111591 | A1 | 5/2012 | Shelton, IV et al. | |
| 2012/0115005 | A1 | 5/2012 | Stulen et al. | |
| 2012/0116380 | A1 | 5/2012 | Madan et al. | |
| 2012/0292367 | A1 | 11/2012 | Morgan et al. | |
| 2012/0305427 | A1* | 12/2012 | Felder | A61L 2/22 53/425 |
| 2013/0009606 | A1 | 1/2013 | Smith et al. | |
| 2016/0059980 | A1* | 3/2016 | Nemec | G06Q 10/0832 422/26 |
| 2019/0201046 | A1 | 7/2019 | Shelton, IV et al. | |
| 2019/0201077 | A1 | 7/2019 | Yates et al. | |
| 2019/0201080 | A1 | 7/2019 | Messerly et al. | |
| 2019/0201091 | A1 | 7/2019 | Yates et al. | |
| 2019/0207857 | A1 | 7/2019 | Shelton, IV et al. | |
| 2019/0274717 | A1 | 9/2019 | Nott et al. | |
| 2019/0311802 | A1 | 10/2019 | Kokubo et al. | |
| 2020/0078114 | A1 | 3/2020 | Asher et al. | |
| 2020/0297973 | A1 | 9/2020 | Blacker et al. | |
| 2021/0284406 | A1* | 9/2021 | McDonald | A61M 5/002 |
| 2021/0330929 | A1* | 10/2021 | Kendrick | A61M 25/002 |
| 2021/0345995 | A1* | 11/2021 | Dobak, III | G01N 1/286 |
| 2023/0013884 | A1 | 1/2023 | Yardibi et al. | |

FOREIGN PATENT DOCUMENTS

| | | | |
|---|---|---|---|
| CN | 105559879 | A | 5/2016 |
| JP | 2014-180498 | A | 9/2014 |
| WO | WO 2016/118196 | A1 | 7/2016 |
| WO | WO 2021/059210 | A1 | 4/2021 |

OTHER PUBLICATIONS

International Search Report and Written Opinion dated Aug. 30, 2023, for International Application No. PCT/IB2023/056627, 16 pages.

International Search Report and Written Opinion dated Oct. 30, 2023, for International Application No. PCT/IB2023/056634, 21 pages.

International Search Report and Written Opinion dated Sep. 1, 2023, for International Application No. PCT/IB2023/056636, 14 pages.

U.S. Appl. No. 62/611,339 entitled "Robot Assisted Surgical Platform," filed Dec. 28, 2017.

U.S. Appl. No. 62/611,340 entitled "Cloud-Based Medical Analytics," filed Dec. 28, 2017.

U.S. Appl. No. 62/611,341 entitled "Interactive Surgical Platform," filed Dec. 28, 2017.

U.S. Appl. No. 17/854,050 entitled, "Surgical Instrument with Predetermined Separation Feature for Waste Stream Utilization and Related Methods," filed Jun. 30, 2022.

U.S. Appl. No. 17/854,065 entitled, "Method of Reclaiming Portions of Surgical Instruments for Remanufacturing and Sustainability," filed Jun. 30, 2022.

U.S. Appl. No. 17/854,104 entitled, "Robotic Surgical System with Removable Portion and Method of Disassembling Same," filed Jun. 30, 2022.

U.S. Appl. No. 17/854,110 entitled, "System for Determining Disposal of Surgical Instrument and Related Methods," filed Jun. 30, 2022.

U.S. Appl. No. 17/854,120 entitled, "Surgical Instrument with Various Alignment Features and Method for Improved Disassembly and Assembly," filed Jun. 30, 2022.

U.S. Appl. No. 17/854,127 entitled, "Surgical System and Methods for Instrument Assessment and Cleaning," filed Jun. 30, 2022.

U.S. Appl. No. 17/854,166 entitled, "Surgical Instrument with Removable Cable and Associated Couplings," filed Jun. 30, 2022.

U.S. Appl. No. 17/854,641 entitled, "Surgical System and Methods of Assembly and Disassembly of Surgical Instrument," filed Jun. 30, 2022.

* cited by examiner

RECLAMATION PACKAGING FOR SURGICAL INSTRUMENT AND RELATED METHODS

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; U.S. Pat. No. 8,663,220, entitled "Ultrasonic Electrosurgical Instruments," issued Mar. 4, 2014, the disclosure of which is incorporated by reference herein, in its entirety; U.S. Pat. No. 10,835,307, entitled "Modular Battery Powered Handheld Surgical Instrument Containing Elongated Multi-Layered Shaft," issued Nov. 17, 2020, the disclosure of which is incorporated by reference herein, in its entirety; and U.S. Pat. No. 11,229,471, entitled "Modular Battery Powered Handheld Surgical Instrument with Selective Application of Energy Based on Tissue Characterization," issued Jan. 25, 2022, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," published on May 2, 2019, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, the disclosure of which is incorporated by reference herein, in its entirety.

Such instruments and robotic surgical systems may be further be incorporated into a surgical system for performing procedures in a surgical environment, such as surgical operating theaters or rooms in a healthcare facility. A sterile field is typically created around the patient and may include properly attired, scrubbed healthcare professions as well as desired furniture and/or fixtures. Examples of such surgical systems and associated features are disclosed in U.S. Pat. Pub. No. 2019/0201046, entitled "Method for Controlling Smart Energy Devices," published on Jul. 4, 2019, the disclosure of which is incorporated by reference herein, in its entirety; U.S. Pat. Pub. No. 2019/0201080, entitled "Ultrasonic Energy Device Which Varies Pressure Applied by Clamp Arm to Provide Threshold Control Pressure at a Cut Progression Location," published on Jul. 4, 2019, the disclosure of which is incorporated by reference herein, in its entirety; U.S. Pat. Pub. No. 2019/0201091, entitled "Radio Frequency Energy Device for Delivering Combined Electrical Signals," published Jul. 4, 2019, the disclosure of which is incorporated by reference herein, in its entirety; U.S. Pat. Pub. No. 2019/0274717, entitled "Methods for Controlling Temperature in Ultrasonic Device," published Sep. 12, 2019, the disclosure of which is incorporated by reference herein, in its entirety; and U.S. Pat. Pub. No. 2019/0207857, entitled "Surgical Network Determination of Prioritization of Communication, Interaction, or Processing Based on System or Device Needs," published Jul. 4, 2019, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
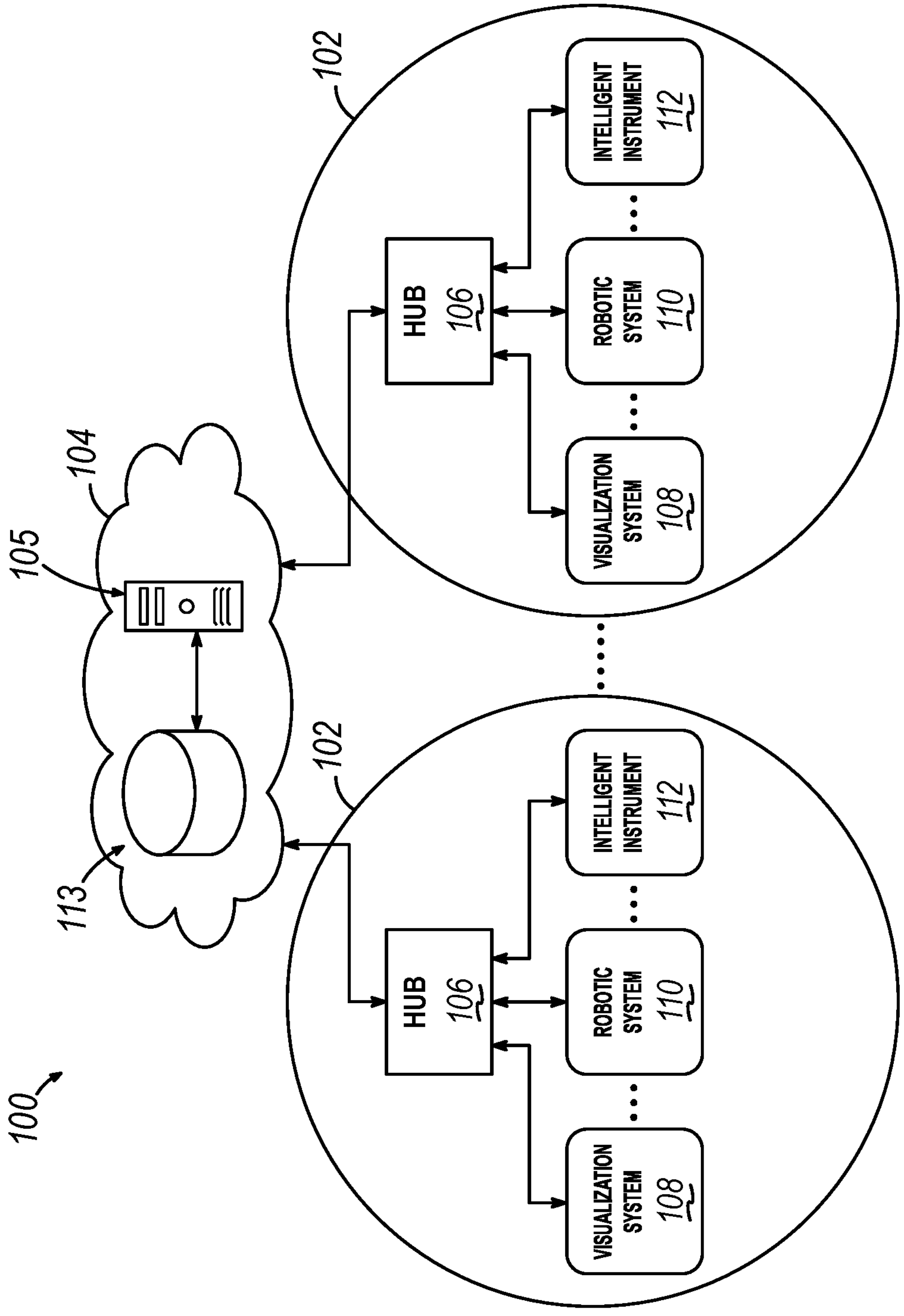
FIG. 1 depicts a block diagram of an example a computer-implemented interactive surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms “proximal” and “distal” are defined herein relative to a human or robotic operator of the surgical instrument. The term “proximal” refers the position of an element closer to the human or robotic operator of the surgical instrument and further away from the surgical end effector of the surgical instrument. The term “distal” refers to the position of an element closer to the surgical end effector of the surgical instrument and further away from the human or robotic operator of the surgical instrument. In addition, the terms “upper,” “lower,” “top,” “bottom,” “above,” and “below,” are used with respect to the examples and associated figures and are not intended to unnecessarily limit the invention described herein.

I. EXAMPLE OF A SURGICAL SYSTEM

With respect to FIG. 1, a computer-implemented interactive surgical system (100) includes one or more surgical systems (102) and a cloud-based system (e.g., a cloud (104) that may include a remote server (113) coupled to a storage device (105)). Each surgical system (102) of the present example includes at least one surgical hub (106) in communication with cloud (104) that may include a remote server (113). In one example, as illustrated in FIG. 1, surgical system (102) includes a visualization system (108), a robotic system (110), and a handheld intelligent surgical instrument (112), which are configured to communicate with one another and/or hub (106). In some aspects, a surgical system (102) may include an M number of hubs (106), an N number of visualization systems (108), an O number of robotic systems (110), and a P number of handheld intelligent surgical instruments (112), where M, N, O, and P are integers greater than or equal to one. In any case, any suitable combination of features provided below may be incorporated into an exemplary surgical system, such as surgical system (100), and used in the surgical theater in order to perform a desired surgical procedure as would be apparent to one skilled in the art in view of the teachings herein.

Figure 2:
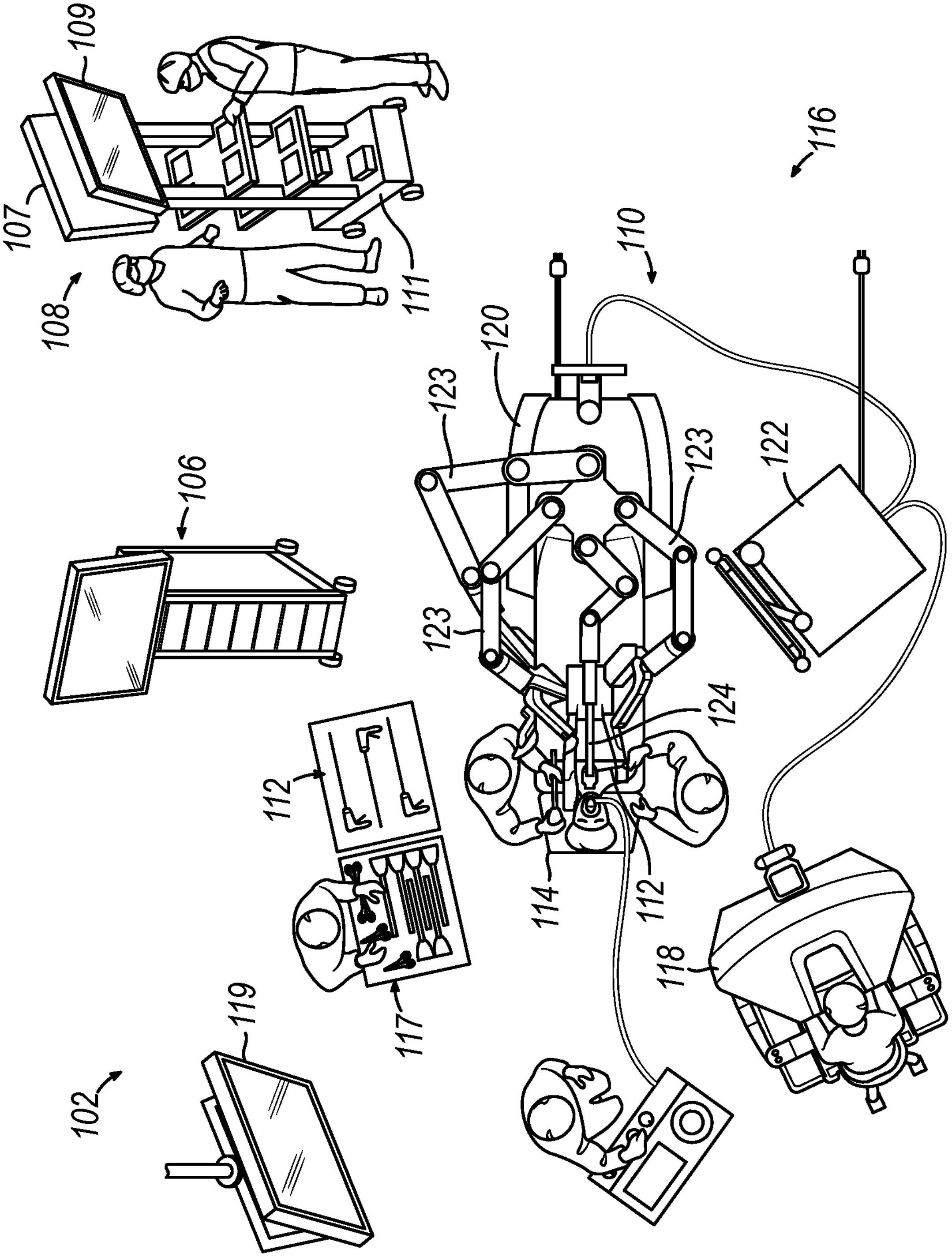
FIG. 2 depicts a top schematic view of an example of a surgical system for performing a surgical procedure in an operating room of a healthcare facility.

FIG. 2 depicts an example of a surgical system (102) being used to perform a surgical procedure on a patient who is lying down on an operating table (114) in a surgical operating room (116). A robotic system (110) is used in the surgical procedure as a part of surgical system (102). Robotic system (110) includes a surgeon’s console (118), a patient side cart (120) (surgical robot), and a surgical robotic hub (122). Patient side cart (120) can manipulate at least one removably coupled surgical tool (117) with any one of a plurality of surgical arms (123) through a minimally invasive incision in the body of the patient while the surgeon views the surgical site through console (118). An image of the surgical site can be obtained by a medical imaging device (124), which can be manipulated by patient side cart (120) to orient imaging device (124). Robotic hub (122) can be used to process the images of the surgical site for subsequent display to the surgeon through console (118).

Other types of robotic systems can be readily adapted for use with surgical system (102). Various examples of robotic systems and surgical tools that are suitable for use with the present disclosure are described in U.S. Provisional Patent Application Ser. No. 62/611,339, entitled “Robot Assisted Surgical Platform,” filed Dec. 28, 2017, the disclosure of which is herein incorporated by reference in its entirety.

Various examples of cloud-based analytics that are performed by cloud (104, and are suitable for use with the present disclosure, are described in U.S. Provisional Patent Application Ser. No. 62/611,340, entitled Cloud-Based Medical Analytics,” filed Dec. 28, 2017, the disclosure of which is herein incorporated by reference in its entirety.

In various aspects, imaging device (124) includes at least one image sensor and one or more optical components. Suitable image sensors include, but are not limited to, Charge-Coupled Device (CCD) sensors and Complementary Metal-Oxide Semiconductor (CMOS) sensors. In various aspects, imaging device (124) is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. Some aspects of spectral and multi-spectral imaging are described in greater detail under the heading "Advanced Imaging Acquisition Module" in U.S. Provisional Patent Application Ser. No. 62/611,341, entitled "Interactive Surgical Platform," filed Dec. 28, 2017, the disclosure of which is herein incorporated by reference in its entirety.

Strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In addition to the introduction of any features of surgical system (100), furniture, or fixtures into the sterile field requiring sterilization, additional complications may result from removal of these features from the sterile field, particularly when such features may have contacted, or presumed to have contacted, the patient, including any tissues and/or fluids associated with the surgical procedure. Such contamination of these features from the patient often requires special consideration during or after the surgical procedure, particularly when processing these features for disposal, reuse, or remanufacturing as desired. In one example, surgical system (100) and/or healthcare professionals associated with the surgical procedure may be specifically equipped to address such processing as discussed below in greater detail.

As illustrated in FIG. 2, a primary display (119) is positioned in the sterile field to be visible to an operator at operating table (114). In addition, a visualization tower (111) is positioned outside the sterile field. Visualization tower (111) includes a first non-sterile display (107) and a second non-sterile display (109), which face away from each other. Visualization system (108), guided by hub (106), is configured to utilize displays (107, 109, 119) to coordinate information flow to operators inside and outside the sterile field. For example, hub (106) may cause visualization system (108) to display a snapshot of a surgical site, as recorded by imaging device (124), on a non-sterile display (107) or (109), while maintaining a live feed of the surgical site on the primary display (119). The snapshot on non-sterile display (107) or display (109) can permit a non-sterile operator to perform a diagnostic step relevant to the surgical procedure, for example.

In one aspect, hub (106) is also configured to route a diagnostic input or feedback entered by a non-sterile operator at visualization tower (111) to primary display (119) within the sterile field, where it can be viewed by a sterile operator at the operating table. In one example, the input can be in the form of a modification to the snapshot displayed on non-sterile display (107) or display (109), which can be routed to primary display (119) by hub (106).

Referring to FIG. 2, a surgical instrument (112) is being used in the surgical procedure as part of surgical system (102). Hub (106) is also configured to coordinate information flow to a display of the surgical instrument (112) such as in, for example, U.S. Provisional Patent Application Ser. No. 62/611,341, entitled "Interactive Surgical Platform," filed Dec. 28, 2017, the disclosure of which is herein incorporated by reference in its entirety. A diagnostic input or feedback entered by a non-sterile operator at visualization tower (111) can be routed by hub (106) to surgical instrument display (115) within the sterile field, where it can be viewed by the operator of surgical instrument (112). Example surgical instruments that are suitable for use with surgical system (102) are described under the heading "Surgical Instrument Hardware" and in U.S. Provisional Patent Application Ser. No. 62/611,341, entitled "Interactive Surgical Platform," filed Dec. 28, 2017, the disclosure of which is herein incorporated by reference in its entirety, for example.

Figure 3:
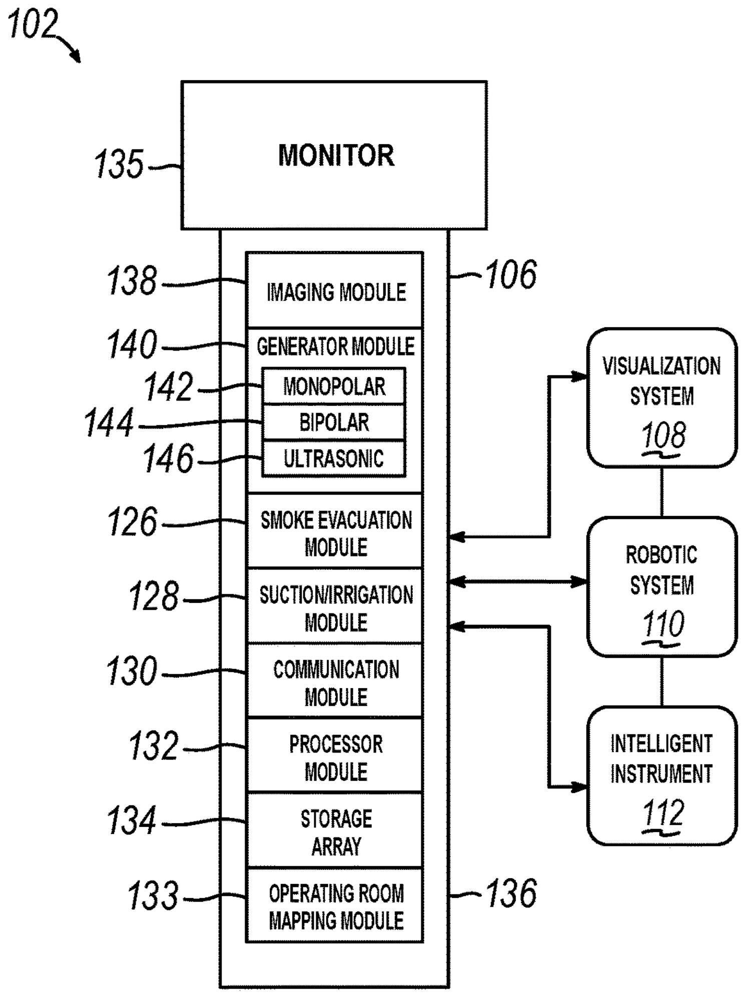
FIG. 3 depicts a side schematic view of an example of a surgical hub of the surgical system of FIG. 2.

Referring now to FIG. 3, a hub (106) is depicted in communication with a visualization system (108), a robotic system (110), and a handheld intelligent surgical instrument (112). Hub (106) includes a hub display (135), an imaging module (138), a generator module (140), a communication module (130), a processor module (132), and a storage array (134). In certain aspects, as illustrated in FIG. 3, hub (106) further includes a smoke evacuation module (126), a suction/irrigation module (128), and/or an operating room mapping module (133).

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure (136) offers a unified environment for managing the power, data, and fluid lines, which reduces the frequency of entanglement between such lines.

Figure 4:
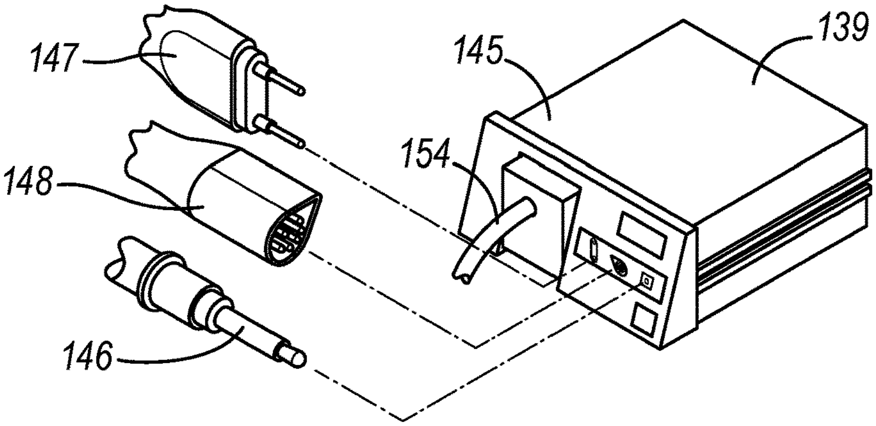
FIG. 4 depicts a perspective view of a combination generator module with bipolar, ultrasonic, and monopolar contacts of the surgical system of FIG. 2.

Referring to FIGS. 3-4, aspects of the present disclosure are presented for a hub modular enclosure (136) that allows the modular integration of a generator module (140), a smoke evacuation module (126), and a suction/irrigation module (128). Hub modular enclosure (136) further facilitates interactive communication between modules (140, 126, 128). As shown in FIG. 4, generator module (140) can be a generator module with integrated monopolar, bipolar, and ultrasonic components supported in a single housing unit (139) slidably insertable into hub modular enclosure (136). As illustrated in FIG. 4, generator module (140) can be configured to connect to a monopolar device (146), a bipolar device (147), and an ultrasonic device (148). Alternatively, generator module (140) may comprise a series of monopolar, bipolar, and/or ultrasonic generator modules that interact through hub modular enclosure (136). Hub modular enclosure (136) can be configured to facilitate the insertion of multiple generators and interactive communication between the generators docked into the hub modular enclosure (136) so that the generators would act as a single generator.

Figure 5:
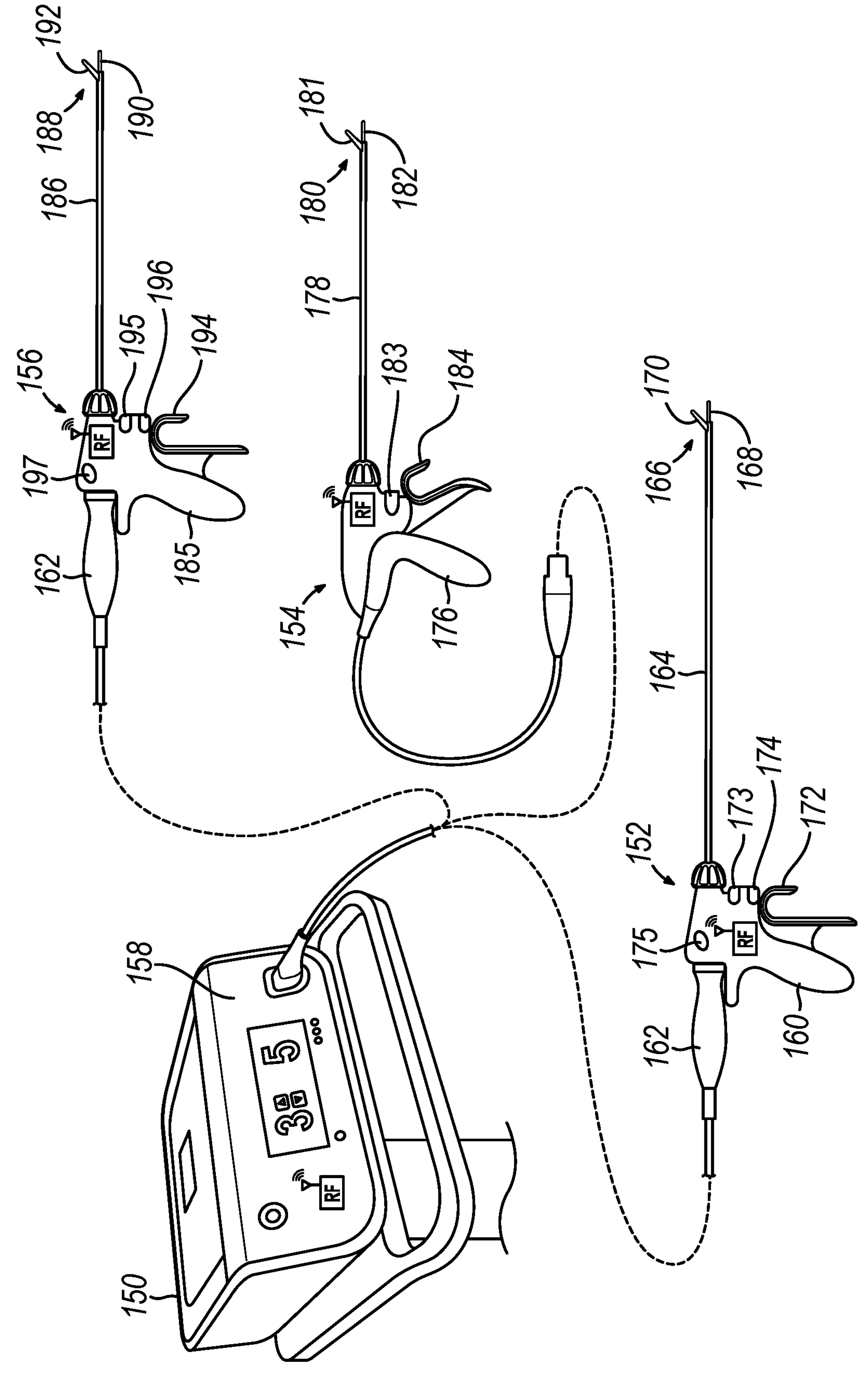
FIG. 5 depicts a side schematic view of an exemplary generator and various examples of surgical instruments for use with the surgical system of FIG. 2.

FIG. 5 illustrates one form of a generator (150) and various surgical instruments (152, 154, 156) usable therewith, where surgical instrument (152) is an ultrasonic surgical instrument (152), surgical instrument (154) is an RF electrosurgical instrument (154), and multifunction surgical instrument (156) is a combination ultrasonic/RF electrosurgical instrument (156). Generator (150) is configurable for use with a variety of surgical instruments. According to various forms, generator (150) may be configurable for use with different surgical instruments of different types including, for example, ultrasonic surgical instruments (152), RF electrosurgical instruments (154), and multifunction surgical instruments (156) that integrate RF and ultrasonic energies delivered simultaneously from generator (150). Although generator (150) of the present example in FIG. 5 is shown separate from surgical instruments (152, 154, 156), generator (150) may alternatively be formed integrally with any of surgical instruments (152, 154, 156) to form a unitary surgical system. Generator (150) comprises an input device (158) located on a front panel of generator (150) console. Input device (158) may comprise any suitable device that generates signals suitable for programming the operation of generator (150). Generator (150) may be configured for wired or wireless communication.

Generator (150) of the present example is configured to drive multiple surgical instruments (152, 154, 156). One example of such surgical instrument is ultrasonic surgical instrument (152) and comprises a handpiece (160), an ultrasonic transducer 162, a shaft assembly (164), and an end effector (166). End effector (166) includes an ultrasonic blade (168) acoustically coupled to ultrasonic transducer (162) and a clamp arm (170). Handpiece (160) has a trigger (172) to operate clamp arm (170) and a combination of toggle buttons (173, 174, 175) to energize and drive ultrasonic blade (168) or other function. Toggle buttons (173, 174, 175) can be configured to energize ultrasonic transducer (162) with generator (150).

Generator (150) also is configured to drive another example of surgical instrument (154). RF electrosurgical instrument (154) includes a handpiece (176), a shaft assembly (178), and an end effector (180). End effector (180) includes electrodes in clamp arms (181, 182) and return through an electrical conductor portion of shaft assembly (178). Electrodes are coupled to and energized by a bipolar energy source within generator (150). Handpiece (176) includes a trigger (183) to operate clamp arms (181, 182) and an energy button (184) to actuate an energy switch to energize electrodes in end effector (180).

Generator (150) also is configured to drive multifunction surgical instrument (156). Multifunction surgical instrument (156) includes a handpiece (185), a shaft assembly (186), and an end effector (188). End effector (188) has an ultrasonic blade (190) and a clamp arm (192). Ultrasonic blade (190) is acoustically coupled to ultrasonic transducer (162). Handpiece (185) has a trigger (194) to operate clamp arm (192) and a combination of toggle buttons (195, 196, 197) to energize and drive ultrasonic blade (190) or other function. Toggle buttons (195, 196, 197) can be configured to energize ultrasonic transducer (162) with generator (150) and energize ultrasonic blade (190) with a bipolar energy source also contained within generator (150). It will be appreciated that handpieces (160, 176, 185) may be replaced with a robotically controlled instrument for incorporating one or more aspects of surgical instruments (152, 154, 156). Accordingly, the term "handpiece" should not be limited to this context and to handheld use.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radiofrequency functions, all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device. Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

II. EXEMPLARY SURGICAL KITS AND METHOD OF PROCESSING A MEDICAL DEVICE

In some instances, it may be desirable to reclaim a portion of a surgical instrument (e.g., surgical instruments (152, 154, 156)) to reduce medical waste, which may reduce the environmental impact and the associated cost. It may be beneficial to separate various components of surgical instrument (152, 154, 156) for added efficiencies. For example, it may be beneficial to process different components differently (e.g., send different components to different locations). For components that are not capable of being reclaimed, it may be desirable to dispose of the component in an environmentally friendly manner. To assist the personnel of a medical facility (e.g., a hospital), it is desirable to make the reclamation process and disposal process as streamlined and straightforward as possible. This may improve the process workflow within an operating room of the medical facility.

A. First Exemplary Surgical Kit

Figure 6:
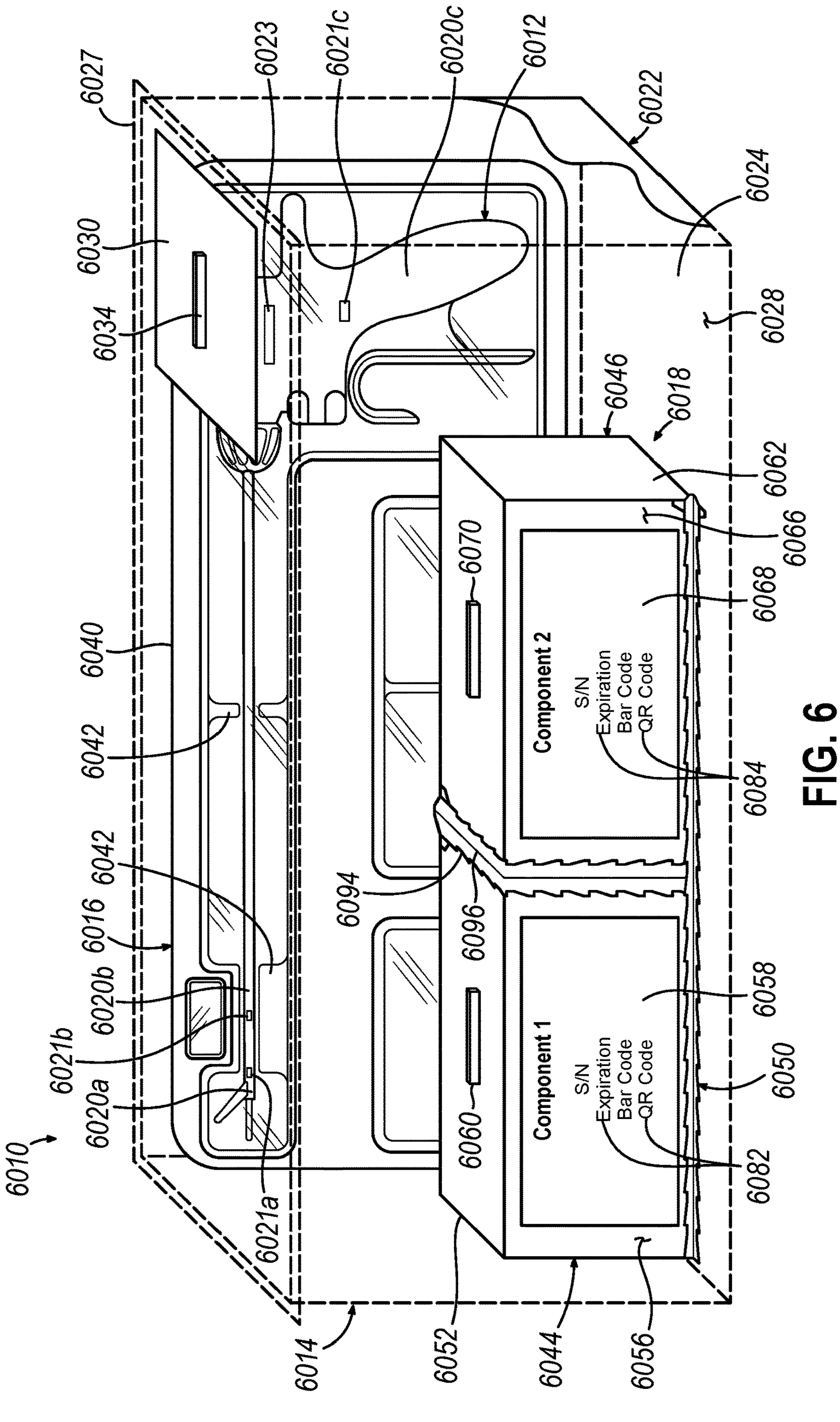
FIG. 6 depicts a perspective schematic view of a first exemplary surgical kit, where an outer packaging of the surgical kit is in a closed configuration.
Figure 7A:
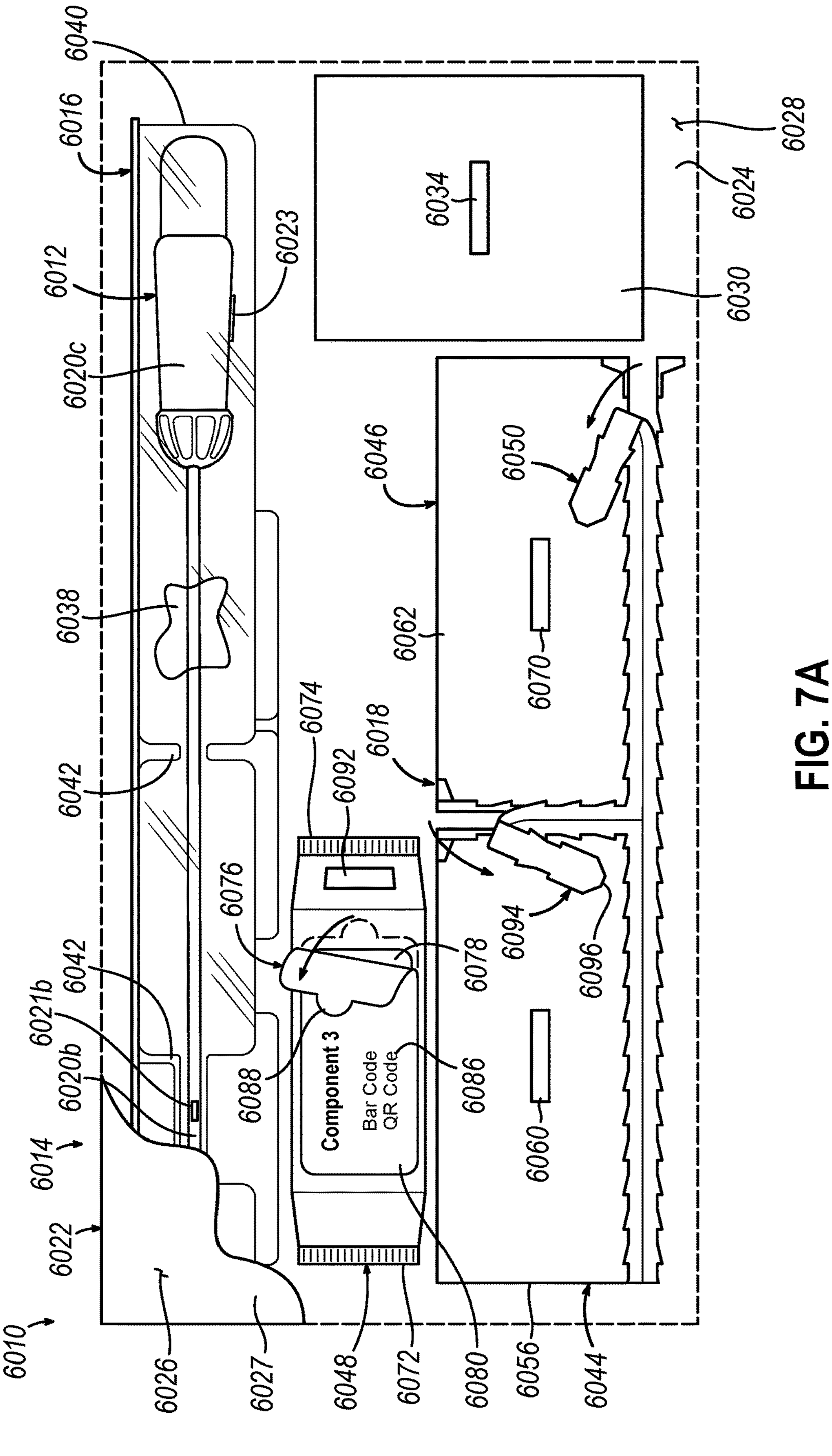
FIG. 7A depicts a top schematic view of the surgical kit of FIG. 6, but with the outer packaging in a partially open configuration.

FIGS. 6-7A show a first exemplary surgical kit (6010) including a surgical instrument (6012), an outer packaging (6014), a sterile packaging (6016), and a return packaging (6018). Surgical kit (6010) may provide initial sterile delivery of surgical instrument (6012) and also packaging for reclamation or disposal of surgical instrument (6012). In some versions, sterile packaging (6016), or even outer packaging (6014), may be reclaimed to minimize contamination during return transport and handling.

Surgical instrument (6012) may be similar to surgical instruments (152, 154, 156) shown in FIG. 5. For example, surgical instrument (6012) may be similar to ultrasonic surgical instrument (152), RF electrosurgical instrument (154), combination ultrasonic/RF electrosurgical instrument (156), or a surgical stapler (not shown). Surgical instrument (6012) may be attachable to a surgical arm (123) of robotic system (110) or may be similar to handheld intelligent surgical instrument (112). Surgical instrument (6012) includes a plurality of portions, shown as first, second, and third portions (6020*a*-*c*), configured to separate from each other. As used herein, portions may refer to different locations of the same component or entirely different components. While first portion (6020*a*) is shown as including the end effector, second portion (6020*b*) is shown as including the shaft, and third portion is shown as including the handle, these are not exclusive. First, second, and third portions (6020*a*-*c*) may refer to a variety of different portions of surgical instrument (6012). While first, second, and third portions (6020*a*-*c*) are shown, more or fewer portions are envisioned. It is also envisioned that certain portions of surgical instrument (6012) may still be disposed of as medical waste, while other portions are reclaimed for subsequent use in a surgical instrument.

First, second, and third portions (6020*a*-*b*) may separate using a variety of different connection structures (e.g., mechanical, electrical, and/or magnetic connection structures). In some versions, first, second, and third portions (6020*a*-*c*) of surgical instrument (6012) may be destructively disassembled (e.g., using a laser or a breaking tool) after use of surgical instrument (6012). For example, breaking tool (not shown) may break first and second portions (6020*a*-*b*) of surgical instrument (6012) along a predetermined break point. As shown, first, second, or third portions (6020*a*-*c*) of surgical instrument (6012) each include a machine readable tag (6021*a*-*c*). As used herein, a machine readable tag is intended to encompass a physical chip (e.g., an RFID chip) as well as an optical code (e.g., a QR code or bar code). As shown, surgical instrument (6012) includes a master machine readable tag (6023), which may be a separate machine readable tag from machine readable tags (6021*a*-*c*). However, one of machine readable tags (6021*a*-*c*) may serve as master machine readable tag (6023). Master machine readable tag (6023) may include information (e.g., the serial number, production date, model number, etc.) pertaining to an entirety of surgical instrument (6012) and/or of specific included portions (e.g., first, second, and third portions (6020*a*-*c*)).

Outer packaging (6014) includes a body (6022) and an optional lid (6027) that define an interior (6024) and an exterior (6026). In the closed configuration of FIG. 6, interior (6024) is completely enclosed. Outer packaging (6014) moves from the closed configuration of FIG. 6 to the open configuration of FIG. 7A when outer packaging (6014) is opened up. In the open configuration, the user may remove sterile packaging (6016) containing surgical instrument (6012). In other words, outer packaging (6014) is opened by the user to expose interior (6024) in the open configuration to allow for access of surgical instrument (6012) for use in the surgical procedure. Interior (6024) of outer packaging (6014) is collectively formed from inner surfaces (6028) of body (6022) and lid (6027).

As shown in FIG. 6, inner surface (6028) of lid (6027) includes a repositionable label (6030) configured to couple with return packaging (6018). Outer packaging (6014) may include a signal blocking feature layer to prevent machine readable tag (6021*a*-*c*, 6023, 6034) from being read by code reader (6438, 6440) (see FIG. 10) when outer packaging (6014) is in the closed configuration. A user may simply remove repositionable label (6030) from lid (6027) of outer packaging (6014) and place repositionable label (6030) on return packaging (6018) which may reduce the time for user to locate, remove, and position repositionable label (6030). Alternatively, repositionable label (6030) may be disposed freely within interior (6024) of outer packaging (6014).

Sterile packaging (6016) is configured to surround surgical instrument (6012). Sterile packaging (6016) includes a body (6036) that defines an interior (6038) (see FIG. 7A) and an exterior (6040). Sterile packaging (6016) is disposed within interior (6024) of outer packaging (6014) in the closed configuration. In some versions, outer packaging (6014) may be omitted, such that return packaging (6018) is coupled with sterile packaging (6016) or is disposed within interior (6038) of sterile packaging (6016). As shown, sterile packaging (6016) includes recessed portions (6042) that complement the size and/or shape of the components.

Return packaging (6018) is configured to receive at least one of first portion (6020*a*), second portion (6020*b*), or third portion (6020*c*) of surgical instrument (6012) after the surgical procedure. Return packaging (6018) may be disposed completely within interior (6024) of outer packaging (6014) in the closed configuration. Optionally, return packaging (6018) may be coupled with outer packaging (6014), coupled with sterile packaging (6016), and/or disposed within interior (6038) of sterile packaging (6016) in the closed configuration. Return packaging (6018) may connect to a specific location of surgical instrument (6012) to improve disassembly. As shown in FIG. 6, return packaging (6018) may be coupled with outer packaging (6014) using a frangible portion (6050) configured to be severed by a user. In some versions, frangible portion (6050) may include a piece of string, which, when pulled, weakens scores frangible portion (6050).

Return packaging (6018) may be segmented to contain separate portions of reclaimed components. Return packaging (6018) may include a plurality of individual return packages. As shown in FIG. 7A, the plurality of individual return packages include first, second, and third return packages (6044, 6046, 6048). However, more or fewer return packages (6044, 6046, 6048) are also envisioned. First return package (6044) includes a body (6052) that defines an interior (6054) (see FIG. 7B) and an exterior (6056). Exterior (6056) includes a repositionable label (6058) and a machine readable tag (6060). Similarly, second return package (6046) includes a body (6062) that defines an interior (6064) (see FIG. 7B) and an exterior (6066). Exterior (6066) includes a repositionable label (6068) and a machine readable tag (6070). Third return package (6048) is shown as a bag with opposing first and second ends (6072, 6074) being sealed. Third return package (6048) includes a resealable flap (6076) configured to allow the user to insert third portion (6020*c*) into an interior (6078). Resealable flap (6076) may include a label (6080).

Each machine readable tag (6060, 6070, 6092) is coupled with at least one of surgical instrument (6012), outer packaging (6014), or return packaging (6018). Code readers (6434, 6436) (see FIG. 10) are configured to read machine readable tag (6060, 6070, 6092) from surgical instrument (6012), outer packaging (6014), or return packaging (6018). For example, return packaging (6018) may include a machine readable tag (6060, 6070, 6092) configured to identify surgical instrument (6012) using code readers (6434, 6436). For example, first, second, and third return packages (6044, 6046, 6048) may also include machine readable tags (6060, 6070, 6092) readable by code readers (6438, 6440). Machine readable tags (6060, 6070, 6092) may be used of in addition to or instead of machine readable tags (6021*a*-*c*, 6023, 6034).

Repositionable labels (6058, 6068) and label (6080) may include an optical code, such as a bar code or a QR code, that is optically readable by code readers (6438, 6440). Repositionable labels (6058, 6068) and label (6080) may include indicia (6082, 6084, 6086) to identify surgical instrument (6012) or first portion (6020*a*), second portion (6020*b*), or third portion (6020*c*) of surgical instrument (6012). For example, indicia (6082, 6084, 6086) may include at least one of a serial number, a model number, and/or an expiration date. Other indicia (6082, 6084, 6086) is also envisioned. For third return package (6048), label (6080) may be attached at one end of resealable flap (6076) and be closeable by coupling terminal end (6088) of resealable flap (6076) to third return package (6048).

In some versions, first return package (6044) may be initially coupled with second return package (6046). As shown in FIGS. 6 and 7A, first and second return packages (6044, 6046) are coupled using a frangible portion (6094). Frangible portion (6094) may be manually severed by a user to maintain sterility. In some versions, frangible portion (6094) may include a piece of string (6096), which, once pulled, weakens and scores frangible portion (6094) along a break line. As shown, third return package (6048) is disposed within interior (6024) of outer packaging (6014), and is not coupled with first and second return packages (6044, 6046).

Figure 7B:
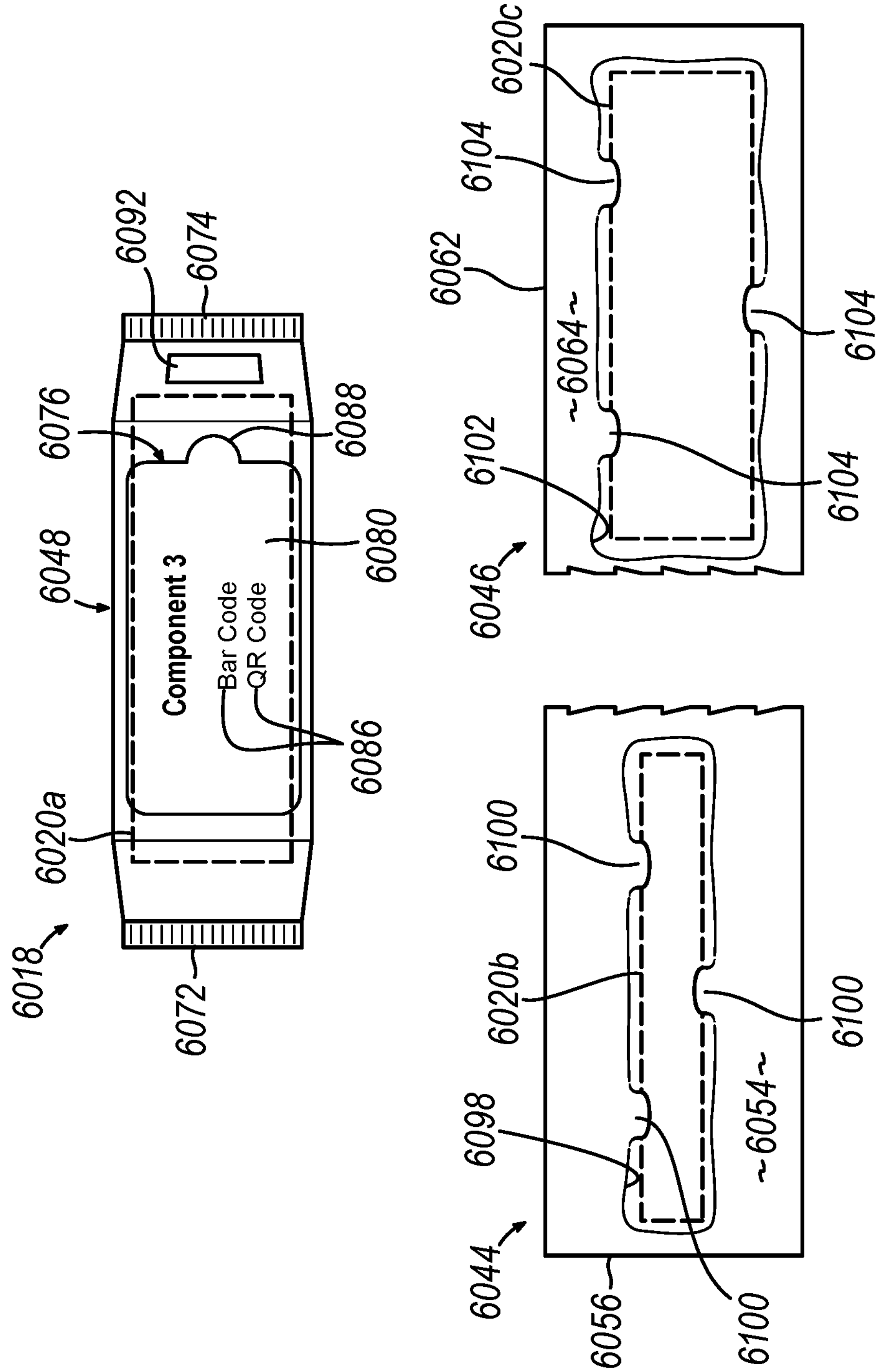
FIG. 7B depicts a top schematic view of return packaging of the surgical kit including portions of the surgical instrument of FIG. 7A.

As shown in FIG. 7B, first return package (6044) portion is configured to receive first portion (6020*a*) of surgical instrument (6012). First return package (6044) includes a recessed portion (6098) and at least one projection, shown as projections (6100). Projections (6100) are configured to positively engage first portion (6020*a*) of surgical instrument (6012). Similarly, second return package (6046) includes a recessed portion (6102) and at least one projection, shown as projections (6104). Projections (6104) are configured to positively engage second portion (6020*b*) of surgical instrument (6012). Projections (6100, 6104) may be integrally formed with respective return packages (6044, 6046), or projections (6100, 6104) may be a separate component coupled with respective return packages (6044, 6046). Third return package (6048) is configured to receive third portion (6020*c*) of surgical instrument (6012). Recessed portions (6098, 6102) of return packaging (6018) may serve a variety of functions. For example, recessed portions (6098, 6102) may provide rigidity to return packaging (6018). Recessed portions (6098, 6102) and projections (6100, 6104) may be shaped and sized to retain first and second portions (6020*a*-*b*) upon disassembly of surgical instrument (6012) after the surgical procedure. Recessed portions (6098, 6102) and projections (6100, 6104) may improve the ability to separate first and second portions (6020*a*-*b*) in a controlled manner.

B. Second Exemplary Surgical Kit

Figure 8:
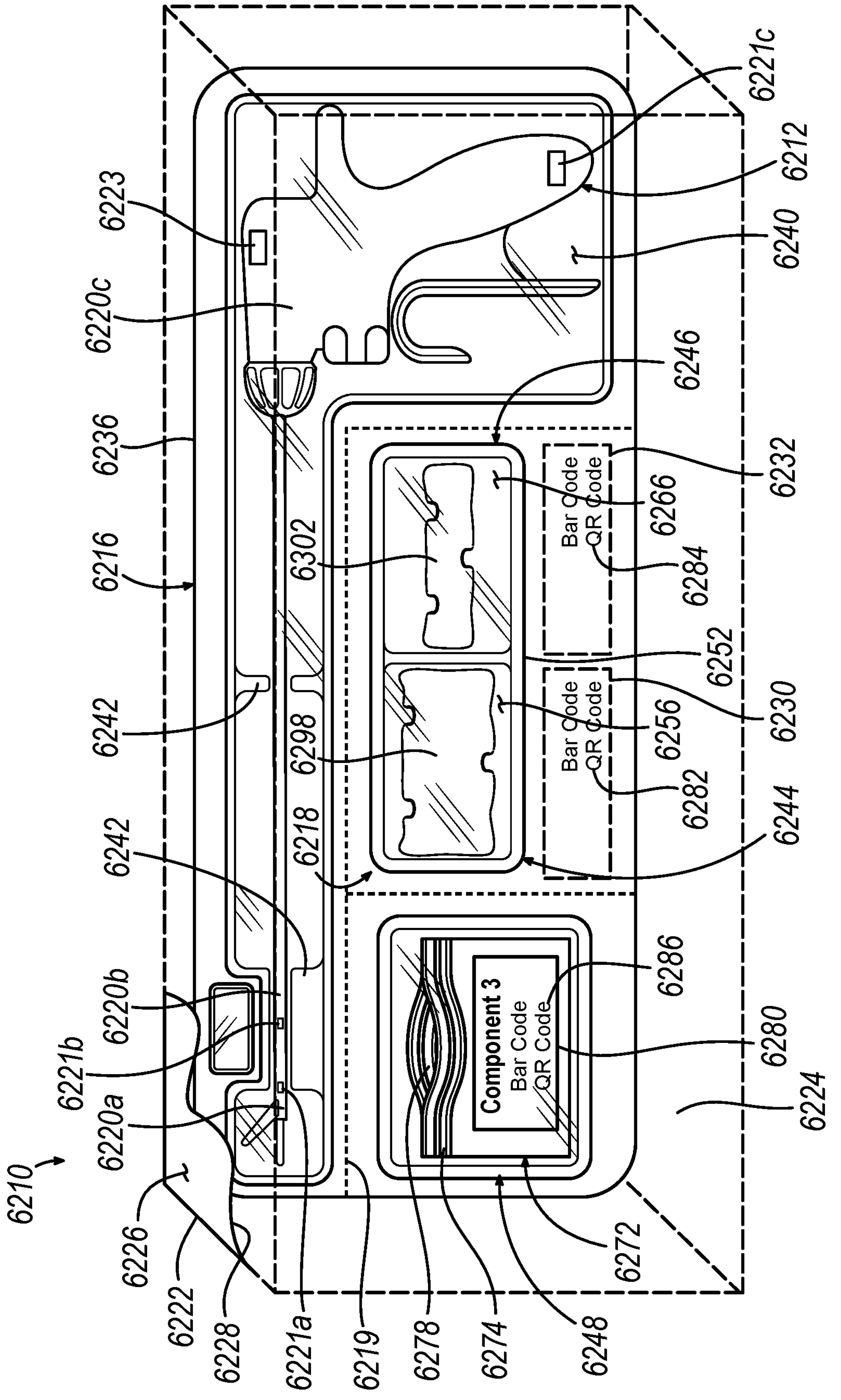
FIG. 8 depicts a perspective schematic view of a second exemplary surgical kit, where the outer packaging of the surgical kit is in a closed configuration.

FIG. 8 shows a second exemplary surgical kit (6210) that includes a surgical instrument (6212), an outer packaging (6214), a sterile packaging (6216), and a return packaging (6218). Surgical kit (6210) is similar to surgical kit (6010) described above with reference to FIGS. 6-7B with differences described in detail below. Unlike sterile packaging (6016), a portion of return packaging (6218) is coupled with sterile packaging (6216) and a portion of return packaging (6218) is disposed within interior (6238) (see FIG. 9) of sterile packaging (6216). In some versions, outer packaging (6214) may be omitted.

Surgical instrument (6212) is similar to surgical instrument (6012). Surgical instrument (6212) includes a plurality of portions, including first, second, and third portions (6220*a*-*c*), configured to separate from each other along a frangible portion (6219). In some versions, at least one of first, second, or third portions (6220*a*-*c*) of surgical instrument (6212) includes a machine readable tag (6221*a*-*c*). Surgical instrument (6212) includes a master machine readable tag (6223) similar to master machine readable tag (6023).

Outer packaging (6214) is similar to outer packaging (6014). Outer packaging (6214) includes a body (6222) that defines an interior (6224) and an exterior (6226). In the closed configuration of FIG. 8, interior (6224) is completely enclosed. Outer packaging (6214) moves from the closed configuration of FIG. 8 to the open configuration of (similar to FIG. 7A) when outer packaging (6214) is opened. Interior (6224) of outer packaging (6214) is formed from inner surfaces (6228) of body (6222).

Sterile packaging (6216) is similar to sterile packaging (6016). Sterile packaging (6216) is configured to surround surgical instrument (6212). Sterile packaging (6216) includes a body (6236) that defines an interior (6238) and an exterior (6240). Sterile packaging (6216) is disposed within interior (6224) of outer packaging (6214) in the closed configuration. As shown, sterile packaging (6216) may include recessed portions (6242) that complement the size and/or shape of the components. Repositionable labels (6230, 6232) may be used to cover and label first and second portions (6220*a-b*) for transport. While not shown, computer readable code may also be included for tracking. A portion of surgical instrument (6212) may be placed back into sterile packaging (6216) after usage.

Figure 9:
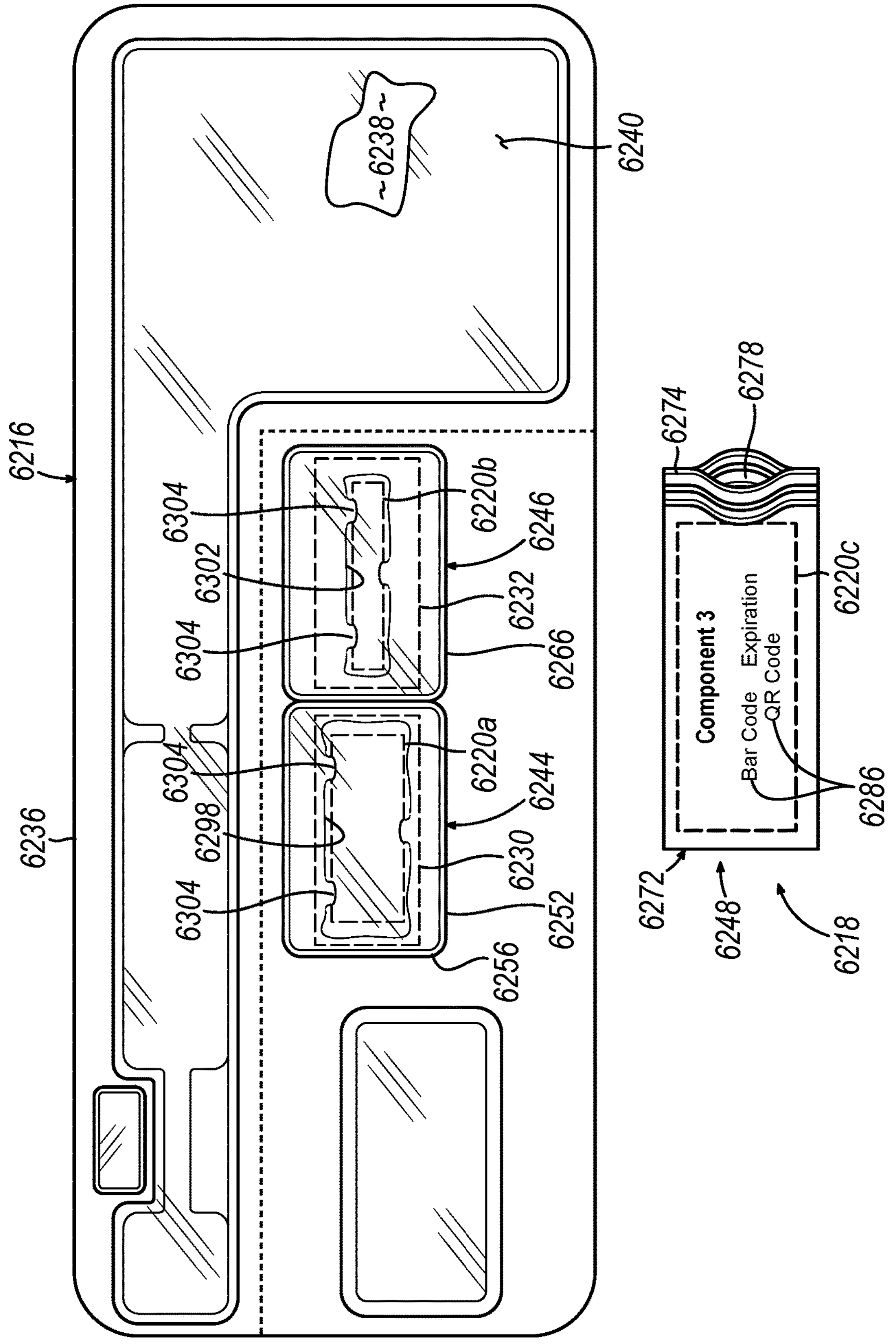
FIG. 9 depicts a top schematic view of sterile packaging, return packaging, and portions of the surgical instrument of the surgical kit of FIG. 8.

Return packaging (6218) is configured to receive at least one of first portion (6220*a*), second portion (6220*b*), or third portion (6220*c*) of surgical instrument (6212) after the surgical procedure. Return packaging (6218) may be segmented to contain separate portions of the returned or recovered components. Return packaging (6218) includes a plurality of individual return packages. As shown in FIG. 8, the plurality of individual return packages includes first, second, and third return packages (6244, 6246, 6248). However, more or fewer return packages are envisioned. First return package (6244) includes a body (6252) that defines an interior (not shown) and an exterior (6256). Similarly, second return package (6246) includes a body (6262) that defines an interior (not shown) and an exterior (6266). FIG. 9 shows repositionable label (6230) affixed to exterior (6256) and repositionable label (6268) affixed to exterior (6266). Repositionable labels (6230, 6232) may include indicia (6282, 6284) similar to indicia (6082, 6084) that act as machine readable tags as described above. While not shown, exteriors (6256, 6266) may include additional machine readable tags.

Third return package (6248) includes a flexible bag (6272). Flexible bag (6272) is configured to allow the user to insert third portion (6220*c*) into an interior (6278) of flexible bag (6272). As shown, flexible bag (6272) includes a label (6280) containing indicia (6286). Return packaging (6218) includes a fluid proof seal (6274) configured to prevent fluid from passing therethrough. Fluid proof seal (6274) is configured to transition from an open configuration to receive surgical instrument (6212) after the surgical procedure to a closed configuration to prevent fluid from exiting return packaging (6218). Indicia (6286) may include one or more of a serial number, an expiration data, and/or a unique identifier that may be marked by surgical robotic hub (122) or recorded by surgical robotic hub (122) to indicate usage, time of use, location of use, etc.

As shown in FIG. 9, first return package (6244) is configured to receive first portion (6220*a*) of surgical instrument (6212). First return package (6244) includes a recessed portion (6298) and at least one projection, shown as projections (6300). Projections (6300) are configured to positively engage first portion (6220*a*) of surgical instrument (6212). Similarly, second return package (6246) includes a recessed portion (6302) and at least one projection shown as projections (6304). Projections (6304) (6300) are configured to positively engage second portion (6220*b*) of surgical instrument (6212). Recessed portions (6298, 6302) retain first and second portions (6220*a-b*) upon disassembly of surgical instrument (6212). Third return package (6248) portion is configured to receive third portion (6220*c*) of surgical instrument (6212), so that third portion (6220*c*) may be handled while minimizing user contamination.

C. Exemplary Method

Figure 10:
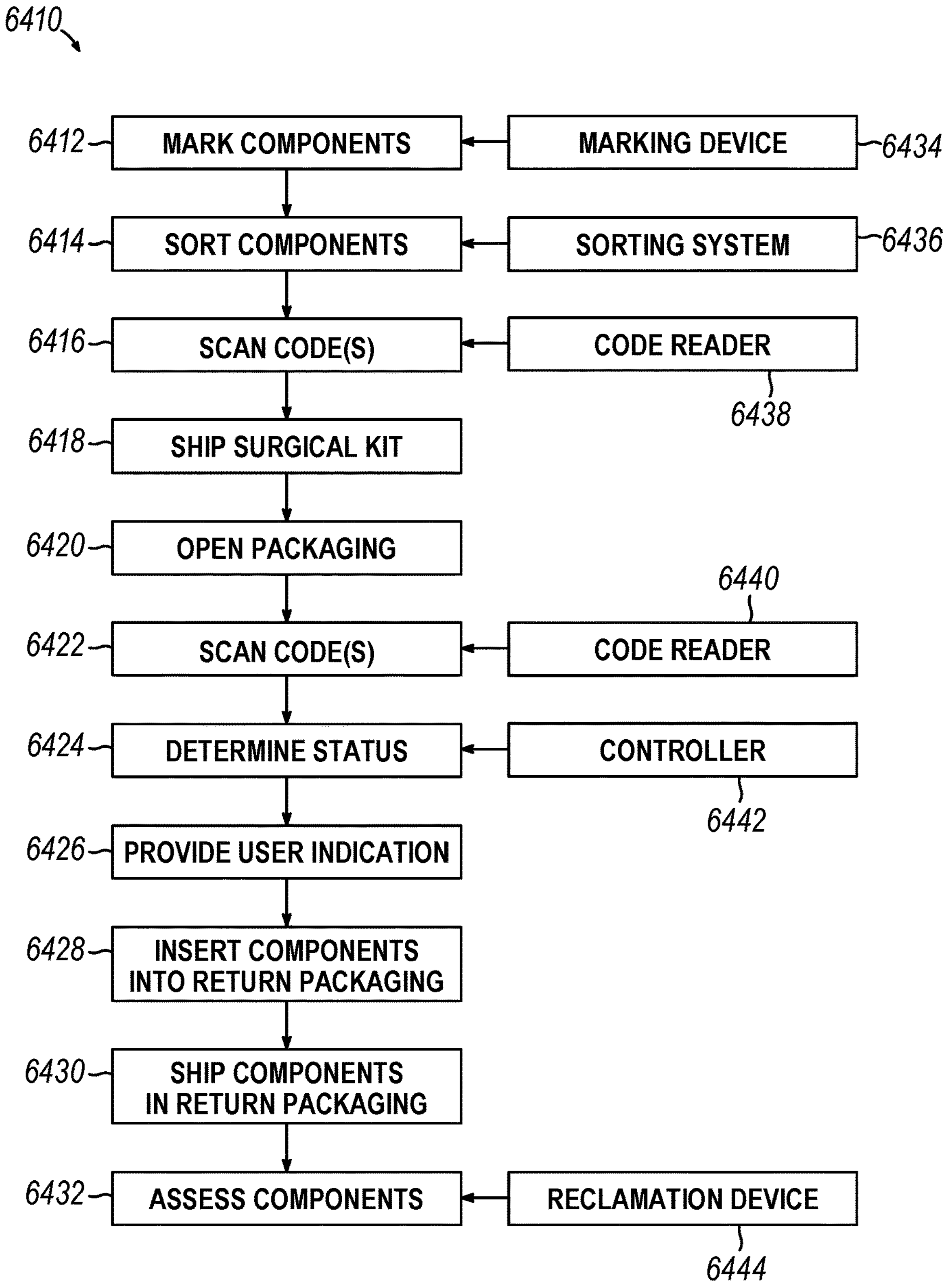
FIG. 10 depicts a diagrammatic view of any exemplary method of using the surgical kits of FIGS. 6 and 8.

A method (6410) of processing a medical device (e.g., surgical instrument (6012, 6212)) is shown and described with reference to FIG. 10. As shown, method (6410) includes steps (6412, 6414, 6416, 6418, 6420, 6422, 6424, 6426, 6428, 6430, 6432). However, more or fewer steps are also envisioned.

At step (6412), method (6410) includes applying at least one machine readable tag (6021*a-c*, 6221*a-c*) to components (e.g., first, second, and third portions (6020*a-c*, 6220*a-c*)) of surgical instruments (6012, 6212) using a marking device (6430). In some versions, marking device (6430) may apply machine readable tag (6021*a-c*, 6221*a-c*) using an indenting process or a laser etching process. While machine readable tag (6021*a-c*, 6221*a-c*) is described as being applied prior to surgical instrument (6012, 6212) being assembled, in some instances, machine readable tag (6021*a-c*, 6221*a-c*) may be applied after surgical instrument (6012, 6212) is assembled. For example, master machine readable tag (6023, 6223) may be applied after surgical instrument (6012, 6212) is assembled.

At step (6414), method (6410) includes sorting and assembling the components for surgical instrument (6012, 6212). For example, the sorting may be performing using a sorting system (6436). Matching reusable components may optimize performance and longevity of surgical instrument (6012, 6212). Sorting system (6436) may include a vision system that may read machine readable tag (6021*a-c*, 6221*a-c*) during this sorting step. An indication may be provided regarding the usability status of the component. The indication may be an alert in the form of audible tone or visual indication. For example, the visual indication may include one or more colored lights on assembly equipment. Machine readable tags (6021*a-c*, 6221*a-c*) indicate specific components (e.g., first, second, and third portions (6020*a-c*, 6220*a-c*)) have been assembled into surgical instrument (6012, 6212). Specific internal components have an electronic chip that identifies specific components that can be read by master machine readable tag (6023). Master machine readable tag (6023, 6223) recognize the components associated with the installation and usage of that surgical instrument (6012, 6212). For example, master machine readable tag (6023) may recognize proximity or at each station of a manufacturing facility there is a camera that recognizes machine readable tag (6021*a-c*, 6221*a-c*) and groups component to surgical instrument (6012, 6212).

At step (6416), method (6410) includes scanning machine readable tags (6021*a-c*, 6023, 6221*a-c*) prior to surgical kits (6010, 6210) leaving the manufacturer. At step (6418), method (6410) includes shipping surgical kit (6010, 6210) to the medical facility for subsequent use.

At step (6420), method (6410) includes opening outer packaging (6014, 6214) and/or sterile packaging (6016, 6216) to transform surgical kit (6010, 6210) from the closed configuration to the open configuration. For example, a user at a medical facility may manually open outer packaging (6014, 6214) and/or sterile packaging (6016, 6216). Sterile packaging (6216) may be removed from outer packaging (6214) in preparation for storage or sterile packaging (6216) may be removed from outer packaging (6214) in prior to being used for a medical procedure. Surgical system (102) may recognize when packaging is opened. For example, after outer packaging (6014, 6214) is opened and surgical instrument (6012, 6212) is removed from outer packaging (6014, 6214), the signal from machine readable tag (6021*a-c*, 6023, 6034, 6221*a-c*, 6223) is no longer blocked by outer packaging (6014, 6214). Until lid (6027) is removed, the signal is blocked or otherwise contained. Once lid (6027) of outer packaging (6014) is removed, signals from machine readable tags (6021*a-c*, 6023, 6034, 6221*a-c*, 6223) may reach surgical robotic hub (122).

At step (6422), method (6410) includes scanning machine readable tag (6021*a-c*, 6023, 6221*a-c*, 6223) using a code reader (6440). Surgical robotic hub (122) or another part of surgical system (102) may include code reader (6440). Code reader (6440) may determine information pertaining to the entirety of surgical instrument (6012, 6212) or a component thereof. This scanning may be manually performed by the user or automatically by surgical robotic hub (122). Machine readable tag (6021*a-c*, 6221*a-c*) may be scanned once surgical instrument (6012, 6212) is assembled into robotic system (110).

At step (6424), method (6410) includes determining the status of the various components. The status may include a coupling status (e.g., whether surgical instrument (6012, 6212) is coupled with robotic system (110)), the condition of the components of surgical instrument (6012, 6212), and their availability to be used. Controller (6442), which may be located in surgical robotic hub (122), may determine use information of first, second, and third portions (6020*a-c*, 6220*a-c*) using the scan from step (6422). Controller (6442) may record this use information on at least one of cloud (104), a surgical robotic hub (122), controller (6442), or machine readable tag (6021*a-c*, 6023, 6034, 6221*a-c*, 6223) for later retrieval. This use data may be transmitted to a central system of the manufacturer of surgical instrument (6012, 6212) and/or a database at the return facility for enhanced tracking.

At step (6426), method (6410) includes providing an indication to the user regarding the coupling status of surgical instrument (6012, 6212). Surgical system (102) may recognize when first, second, and third portions (6020*a-c*, 6220*a-c*) have been used. Surgical system (102) may recognize that the component make of the specific surgical instrument (6012, 6212) is acceptable or unacceptable and may prevent installation if unacceptable. The indication may be an alert in the form of audible tone or visual indication.

At step (6428), method (6410) includes inserting the components into return packaging (6018, 6218). In some versions, a packing tray (which may be formed from a portion of sterile packaging (6216) or a separate tray) may be used to assist with filling of first, second, and third return packages (6044, 6046, 6048, 6244, 6246, 6248) and/or prevent spillage of contents (e.g., first, second, and third portions (6020*a-c*, 6220*a-c*)) placed within first, second, and third return packages (6044, 6046, 6048, 6244, 6246, 6248). The packing tray may improve organization and reduce the overall time to prepare for subsequent shipping of first, second, and third return packages (6044, 6046, 6048, 6244, 6246, 6248) at step (6430).

At step (6432), method (6410) includes assessing returned portions of surgical instrument (6012, 6212). Assessing returned components (e.g., first, second, and third portions (6020*a-c*, 6220*a-c*)), improves process flow so that the components may be assessed and possibly reused. For example, reclamation system (6444) may mark surgical instrument (6012, 6212) to track usages. Tracking may allow for more straightforward sorting of components (e.g., first, second, and third portions (6020*a-c*, 6220*a-c*)) at the return location (e.g., manufacturing facility or other return facility). The return location may scan machine readable tag (6021*a-c*, 6221*a-c*) and sort the component (e.g., first, second, and third portions (6020*a-c*, 6220*a-c*)) according to a variety of criteria, including the number of uses. Reclamation system (6444) may read usage information from surgical instrument (6012, 6212). This usage data may be on a memory (e.g., an EEPROM). Reclamation system (6444) may determine whether surgical instrument (6012, 6212) has been used or not. The memory may store record data pertaining to the use of surgical instrument (6012, 6212) and record component serial numbers. In some versions, surgical instrument (6012, 6212) may be physical marked as described in step (6412).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical kit comprising: (a) a surgical instrument; (b) a packaging that defines an interior and an exterior in a closed configuration, wherein the surgical instrument is disposed within the interior of the packaging or coupled with the packaging in the closed configuration, wherein the packaging is configured to transition to an open configuration by a user to expose the interior and allow for access of the surgical instrument during a surgical procedure; and (c) a return packaging configured to receive at least a portion of the surgical instrument after the surgical procedure for reduced cross-contamination, wherein the return packaging is at least one of coupled with the packaging or disposed within the interior in the closed configuration.

Example 2

The surgical kit of Example 1, wherein the packaging includes an outer packaging, wherein the return packaging disposed within the interior of the outer packaging in the closed configuration.

Example 3

The surgical kit of Example 2, wherein the return packaging includes a machine-readable code configured to identify the surgical instrument using a code reader, wherein the outer packaging includes a signal blocking feature configured to prevent the machine-readable code from being read using the code reader in the closed configuration.

Example 4

The surgical kit of any of Examples 2 through 4, wherein the return packaging includes an interior and an exterior, wherein the interior of the outer packaging is formed from a plurality of inner surfaces, wherein an inner surface of the plurality of surfaces includes a repositionable label configured to be coupled with the exterior of the return packaging.

Example 5

The surgical kit of any of Examples 2 through 4, wherein the packaging includes a sterile packaging configured to surround the surgical instrument, wherein the sterile packaging is disposed within the interior of the outer packaging in the closed configuration.

Example 6

The surgical kit of Example 5, wherein the return packaging is coupled with the sterile packaging or disposed within an interior of the sterile packaging.

Example 7

The surgical kit of any of Examples 1 through 6, wherein the return packaging includes at least one projection configured to positively engage the portion of the surgical instrument.

Example 8

The surgical kit of any of Examples 1 through 7, wherein the return packaging includes indicia configured to identify the surgical instrument.

Example 9

The surgical kit of Example 8, wherein the return packaging includes a repositionable label, wherein the repositionable label includes the indicia.

Example 10

The surgical kit of any of Examples 1 through 9, wherein the return packaging includes a fluid proof seal configured to transition from an open configuration to receive the surgical instrument after the surgical procedure to a closed configuration to prevent fluid from exiting the return packaging.

Example 11

The surgical kit of any of Examples 1 through 10, wherein the return packaging is coupled with the packaging using a frangible portion configured to be severed by a user.

Example 12

The surgical kit of any of Examples 1 through 11, wherein the surgical instrument includes first and second portions configured to separate from each other, wherein the return packaging includes first and second return packages, wherein the first return package is configured to receive the first portion of the surgical instrument, wherein the second return package is configured to receive the second portion of the surgical instrument.

Example 13

The surgical kit of Example 12, wherein the first return package is configured to positively engage the first portion of the surgical instrument, wherein the second return package is configured to positively engage the second portion of the surgical instrument.

Example 14

The surgical kit of Example 12, wherein the first return package is coupled with the second return package.

Example 15

The surgical kit of any of Examples 1 through 14, further comprising a robotic surgical system, wherein the robotic surgical system includes an arm configured to couple with the surgical instrument.

Example 16

A robotic surgical system comprising: (a) a surgical instrument; (b) a packaging that defines an interior and an exterior in a closed configuration, wherein the surgical instrument is disposed within the interior of the packaging or coupled with packaging in the closed configuration, wherein the outer packaging is configured to be opened by a user to expose the interior in an open configuration to allow for access of the surgical instrument during a surgical procedure; (c) a return packaging configured to receive the surgical instrument after the surgical procedure for reduced cross-contamination; (d) machine-readable code coupled with at least one of the surgical instrument, the outer packaging, or the return packaging; and (e) a code reader configured to read the machine-readable code.

Example 17

The robotic surgical system of Example 16, wherein the packaging includes an outer packaging, wherein the return packaging disposed within the interior of the outer packaging in the closed configuration.

Example 18

The robotic surgical system of any of Examples 16 through 17, wherein the outer packaging includes a signal blocking feature configured to prevent the machine-readable code from being read by the code reader in the closed configuration.

Example 19

A method of reclaiming a surgical instrument, the method comprising: (a) opening a packaging material to expose a surgical instrument and a return packaging contained within the packaging material; (b) determining a portion of the surgical instrument is reusable; (c) inserting the portion of the surgical instrument into the return packaging; and (d) enclosing the return packaging.

Example 20

The method of Example 19, further comprising attaching a repositionable label to the return packaging.

IV. MISCELLANEOUS

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/854,065, entitled "Method of Reclaiming Portions of Surgical Instruments for Remanufacturing and Sustainability," filed on even date herewith, the disclosure of which is incorporated by reference herein. Various suitable ways in which the teachings herein may be combined with the teachings of U.S. patent application Ser. No. 17/854,065 will be apparent to those of ordinary skill in the art in view of the teachings herein.

In addition to the foregoing, the teachings herein may be readily combined with the teachings of U.S. patent application Ser. No. 17/854,050, entitled "Surgical Instrument with Predetermined Separation Features for Waste Stream Utilization and Related Methods," filed on even date herewith, the disclosure of which is incorporated by reference herein. Various suitable ways in which the teachings herein may be combined with the teachings of U.S. patent application Ser. No. 17/854,050 will be apparent to those of ordinary skill in the art in view of the teachings herein.

In addition to the foregoing, the teachings herein may be readily combined with the teachings of U.S. patent application Ser. No. 17/854,166, entitled "Surgical Instrument with Removable Cable and Associated Couplings," filed on even date herewith, the disclosure of which is incorporated by reference herein. Various suitable ways in which the teachings herein may be combined with the teachings of U.S. patent application Ser. No. 17/854,166 will be apparent to those of ordinary skill in the art in view of the teachings herein.

In addition to the foregoing, the teachings herein may be readily combined with the teachings of U.S. patent application Ser. No. 17/854,641, entitled "Surgical System and Methods of Assembly and Disassembly of Surgical Instrument," filed on even date herewith, the disclosure of which is incorporated by reference herein. Various suitable ways in which the teachings herein may be combined with the teachings of U.S. patent application Ser. No. 17/854,641 will be apparent to those of ordinary skill in the art in view of the teachings herein.

In addition to the foregoing, the teachings herein may be readily combined with the teachings of U.S. patent application Ser. No. 17/854,104, entitled "Robotic Surgical System with Removable Portion and Method of Disassembling Same," filed on even date herewith, the disclosure of which is incorporated by reference herein. Various suitable ways in which the teachings herein may be combined with the teachings of U.S. patent application Ser. No. 17/854,104 will be apparent to those of ordinary skill in the art in view of the teachings herein.

In addition to the foregoing, the teachings herein may be readily combined with the teachings of U.S. patent application Ser. No. 17/854,110, entitled "System for Determining Disposal of Surgical Instrument and Related Methods," filed on even date herewith, the disclosure of which is incorporated by reference herein. Various suitable ways in which the teachings herein may be combined with the teachings of U.S. patent application Ser. No. 17/854,110 will be apparent to those of ordinary skill in the art in view of the teachings herein.

In addition to the foregoing, the teachings herein may be readily combined with the teachings of U.S. patent application Ser. No. 17/854,120, entitled "Surgical Instrument with Various Alignment Features and Methods for Improved Disassembly and Assembly," filed on even date herewith, the disclosure of which is incorporated by reference herein. Various suitable ways in which the teachings herein may be combined with the teachings of U.S. patent application Ser. No. 17/854,120 will be apparent to those of ordinary skill in the art in view of the teachings herein.

In addition to the foregoing, the teachings herein may be readily combined with the teachings of U.S. patent application Ser. No. 17/854,127, entitled "Surgical System and Methods for Instrument Assessment and Cleaning," filed on even date herewith, the disclosure of which is incorporated by reference herein. Various suitable ways in which the teachings herein may be combined with the teachings of U.S. patent application Ser. No. 17/854,127 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical kit comprising:

(a) a surgical instrument that includes first and second portions configured to separate from each other;

(b) a packaging that defines an interior and an exterior in a closed configuration, wherein the surgical instrument is disposed within the interior of the packaging or coupled with the packaging in the closed configuration, wherein the packaging is configured to transition to an open configuration by a user to expose the interior and allow for access of the surgical instrument during a surgical procedure; and (c) a return packaging configured to receive at least the first and second portions of the surgical instrument after the surgical procedure for reduced cross-contamination, wherein the return packaging is at least one of coupled with the outer packaging or disposed within the interior in the closed configuration, wherein the return packaging comprises:

(i) a first return package configured to receive the first portion of the surgical instrument, wherein the first return package includes at least one projection configured to positively engage the first portion, and (ii) a second return package configured to receive the second portion of the surgical instrument, wherein the second return package includes at least one projection configured to positively engage the second portion.

2. The surgical kit of claim 1, wherein the packaging includes an outer packaging, wherein the outer packaging includes an interior, wherein the return packaging is disposed within the interior of the outer packaging in the closed configuration.

3. The surgical kit of claim 2, wherein the return packaging includes a machine-readable code configured to identify the surgical instrument using a code reader, wherein the outer packaging includes a signal blocking feature configured to prevent the machine-readable code from being read using the code reader in the closed configuration.

4. The surgical kit of claim 2, wherein the return packaging includes an interior and an exterior, wherein the interior of the outer packaging is formed from a plurality of inner surfaces, wherein an inner surface of the plurality of surfaces includes a repositionable label configured to be coupled with the exterior of the return packaging.

5. The surgical kit of claim 2, wherein the packaging includes a sterile packaging configured to surround the surgical instrument, wherein the sterile packaging is disposed within the interior of the outer packaging in the closed configuration.

6. The surgical kit of claim 5, wherein the return packaging is coupled with the sterile packaging or disposed within an interior of the sterile packaging.

7. The surgical kit of claim 5, wherein the return packaging is coupled with the sterile packaging using a frangible portion configured to be severed by a user.

8. The surgical kit of claim 1, wherein the return packaging includes indicia configured to identify the surgical instrument.

9. The surgical kit of claim 1, wherein the return packaging includes a fluid proof seal configured to transition from an open configuration to receive the surgical instrument after the surgical procedure to a closed configuration to prevent fluid from exiting the return packaging.

10. The surgical kit of claim 1, wherein the first return package is coupled with the second return package using a frangible portion configured to be severed by a user.

11. A robotic surgical system comprising:

(a) the surgical kit of claim 1; and (b) an arm configured to couple with the surgical instrument.

12. The surgical kit of claim 1, wherein the at least one projection of the first return package includes a plurality of projections, wherein the at least one projection of the second return package includes a plurality of projections.

13. The surgical kit of claim 12, wherein the plurality of projections of the first return package have a different arrangement than the plurality of projections of the second return package.

14. The surgical kit of claim 1, wherein the first and second portions of the surgical instrument have different dimensions.

15. A robotic surgical system comprising:

(a) a surgical instrument;

(b) a robotic arm configured to couple with the surgical instrument;

(c) a packaging that defines an interior and an exterior in a closed configuration, wherein the surgical instrument is disposed within the interior of the packaging or coupled with the packaging in the closed configuration, wherein the packaging is configured to be opened by a user to expose the interior in an open configuration to allow for access of the surgical instrument during a surgical procedure;

(d) a return packaging configured to receive the surgical instrument after the surgical procedure for reduced cross-contamination;

(e) a machine-readable code coupled with at least one of the surgical instrument, the packaging, or the return packaging;

(f) a code reader configured to read the machine-readable code; and (g) an indicia marking device configured to apply an indicia to the return packaging with the indicia including at least one of a serial number, an expiration data, a unique identifier, a usage, a time of use, or a location of use.

16. The robotic surgical system of claim 15, wherein the packaging includes an outer packaging, wherein the outer packaging includes an interior, wherein the return packaging is disposed within the interior of the outer packaging in the closed configuration.

17. The robotic surgical system of claim 16, wherein the outer packaging includes a signal blocking feature configured to prevent the machine-readable code from being read by the code reader in the closed configuration.

18. The robotic surgical system of claim 15, wherein the surgical instrument includes first and second portions configured to separate from each other, wherein the return packaging comprises: a first return package configured to receive the first portion of the surgical instrument, wherein the first return package includes at least one projection configured to positively engage the first portion, and a second return package configured to receive the second portion of the surgical instrument, wherein the second return package includes at least one projection configured to positively engage the second portion.

19. A method of reclaiming a surgical instrument, the method comprising:

(a) opening a packaging material to expose a surgical instrument and a return packaging contained within the packaging material;

determining first and second portions of the surgical instrument (b) are reusable;

(c) inserting the first portion of the surgical instrument into an interior of a first return package of the return packaging and the second portion of the surgical instrument into an interior of a second return package while the first and second return packages are coupled together; and (d) enclosing the first and second return packages of the return packaging so that the interiors of the first and second packages are separate and discrete from one another.

20. The method of claim 19, further comprising marking the return packaging with indicia including at least one of a serial number, an expiration data, a unique identifier, a usage, a time of use, or a location of use.

* * * * *